United States Patent [19]
Zeelen et al.

[11] 4,186,142
[45] Jan. 29, 1980

[54] CYCLIZATION SUBSTRATES AND 6α-SUBSTITUTED 19-NORSTEROID DERIVATIVES

[75] Inventors: Filippus J. Zeelen, Heesch; Marinus B. Groen, Schayk, both of Netherlands

[73] Assignee: Akzona Incorporated, Asheville, N.C.

[21] Appl. No.: 880,153

[22] Filed: Feb. 22, 1978

[30] Foreign Application Priority Data

Feb. 24, 1977 [NL] Netherlands .......................... 7701971

[51] Int. Cl.$^2$ .............................................. C07J 0/00
[52] U.S. Cl. .......................... 260/397.5; 260/239.55 R; 260/340.9 R; 260/346.11; 260/347.91; 260/448.2 B; 260/586 R; 260/600 R; 560/138; 560/255; 568/592
[58] Field of Search ...................................... 260/397.5; /Steroids MS File

[56] References Cited
FOREIGN PATENT DOCUMENTS
1448873 9/1976 United Kingdom ................ 260/239.55

OTHER PUBLICATIONS
Applegweig, Steroid Drugs, McGraw-Hill (1962) p. 461.

*Primary Examiner*—Ethel G. Love
*Attorney, Agent, or Firm*—Robert H. Falk; Charles A. Wendel; Francis W. Young

[57] ABSTRACT

Novel cyclization substrates of the formula:

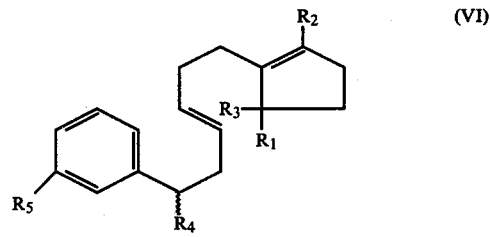

(VI)

wherein:
(a) $R_1$ is H or alkyl of one to four carbons;
(b) $R_2$ is H or alkyl of one to four carbons, with the proviso that $R_1$ is H when $R_2$ is alkyl; and with the proviso that $P_2$ is H when $R_1$ is alkyl;
(c) $R_3$ is a leaving group selected from the group consisting of OH, alkoxy of one to four carbons, alkoxyalkyoxy of from two to about four carbons, acyloxy of from about one to about seven carbons, and trialkylsilyloxy;
(d) $R_4$ is halogen, alkoxy of from one to four carbons, hydrocarbyl of from one to about four carbons, hydrocarbyl of from one to about four carbons substituted by one or more (1) halogens or (2) alkoxy moieties of from one to two carbons; and
(e) $R_5$ is H, alkyl of one to six carbons, hydroxy, or an esterified or estherified moiety of (1) less than eight carbons selected from the group consisting of alkoxy, trialkylsilyloxy, aralkyloxy, cyclo-alkoxy, and heterocyclo-oxy radicals; (2) α-alkoxyalkoxy of from two to four carbons, and (3) acyloxy of from one to seven carbons;

leads by way of a cyclization step to 6α-substituted steroidal derivatives of the formula:

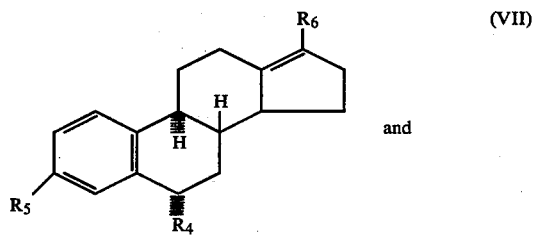

(VII)

and

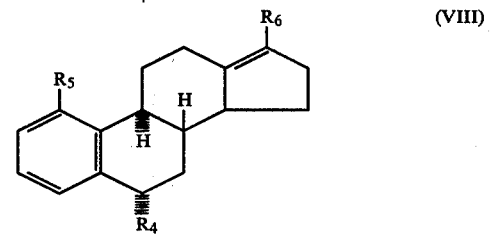

(VIII)

wherein $R_4$ and $R_5$ have the meaning above and $R_6$ is alkyl of from one to about four carbons.

The compounds of the formulae VI, VII and VIII are important intermediates for preparing wellknown biologically active 6α-substituted steroids.

3 Claims, No Drawings

CYCLIZATION SUBSTRATES AND 6α-SUBSTITUTED 19-NORSTEROID DERIVATIVES

BACKGROUND TO THE INVENTION

1. Field of the Invention

The invention relates to (1) the preparation of biologically active cyclisation substrates for steroidal compounds, and (2) to the conversion of these cyclisation substrates into novel steroidal compounds, in particular 6-substituted steroids of the oestrane series.

2. Related Applications

This application is related by structure to another application, Ser. No. 880,151, filed concurrently herewith.

DESCRIPTION OF PRIOR ART AND OTHER INFORMATION

Biologically active 6α-alkyl and 6α-halo compounds of the oestrane and 13-ethylgonane series are known to those in the art; it is therefore important that a good method of synthesis is available for the preparation of these compounds.

The following stereo-selective synthesis was described in 22 Tetrahedon at 1019–1025 (1966)

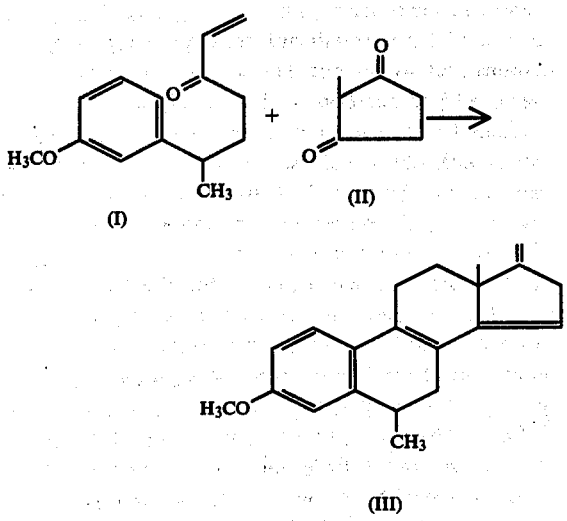

The main product obtained was the 6β-methyl compound (yield 25%–40% by weight) in addition to traces of the 6α-methyl compound. Since the 6α-methyl compounds are the most valuable, attempts were made to isomerise the 6β-methyl compounds to 6α-methyl compounds, after the A-ring had been converted to a 3-oxo-Δ⁴-system:

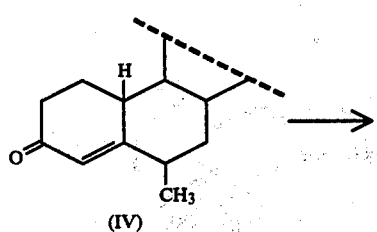

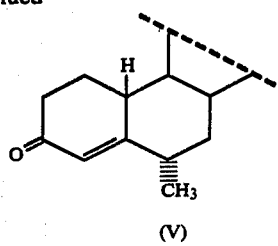

This isomerisation occurs only in part, and the 6α-methyl compound can only be obtained in low yield by this route. The circuitous route via the enol acetate gives higher yields (see 90 Recueil 849 (1971)).

Related art includes U.S. Pat. No. 3,137,689 to Dorfmann et al, which teaches preparation of 6α-methyl-pregnenolones (anti-ovulatory activity); U.S. Pat. No. 3,257,427 to Bowers for 6-alkyl-3-desoxy-$\Delta^{1,3,5(10)}$ estratriene substituted in the 17 position by keto or hydroxy (anti-androgenic action, low feminizing effects; for fertility control and menstrual disorders); U.S. Pat. No. 3,816,481 to Douglas et al. for 6α-methyl-4-gonenes (progestational activity); and British Patent No. 1,448,873 (cyclisation of (arylhexenyl)-cyclopentenols to $\Delta^{1,3,5(10),13(17)}$ gonatetraenes unsubstituted in position 6).

SUMMARY OF THE INVENTION

Surprisingly, it has now been found that biologically active 6α-substituted 19-norsteroids may be obtained by cyclisation of compounds with formula VI:

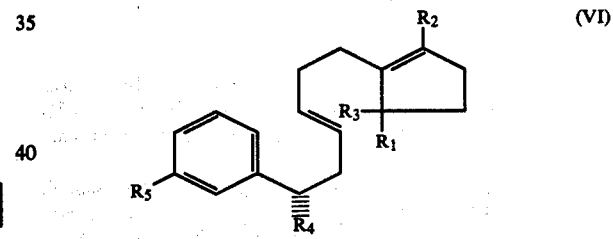

wherein:
(a) $R_1$ is H or alkyl of one to four carbons;
(b) $R_2$ is H or alkyl of one to four carbons, with the proviso that $R_1$ is H when $R_2$ is alkyl; and with the proviso that $R_2$ is H when $R_1$ is alkyl;
(c) $R_3$ is a leaving group selected from the group of OH, alkoxy of from one to about four carbons, alkoxyalkoxy of from two to about four carbons, acyloxy of from about one to about seven carbons, and trialkylsilyloxy of 3–12 carbons;
(d) $R_4$ is halogen, alkoxy of one to four carbons, hydrocarbyl of from one to about four carbons, hydrocarbyl of from one to about four carbons substituted by one or more (1) halogens or (2) alkoxy moieties of from one to two carbons; and
(e) $R_5$ is H, alkyl of one to six carbons, hydroxy, or an esterified or etherified moiety of (1) less than eight carbons selected from the group consisting of alkoxy, trialkylsilyloxy, aralkyloxy, cyclo-alkoxy, and heterocyclo-oxy radicals, (2) α-alkoxyalkoxy of from two to four carbons, and (3) acyloxy of from one to about seven carbons. The cyclisation step takes place at a temperature lower than room temperature (and preferably between about +10° C.

and −100° C.) in the presence of a suitable solvent and an effective amount of an aprotic or protic Lewis acid, resulting sterospecifically in the formation of the isomers:

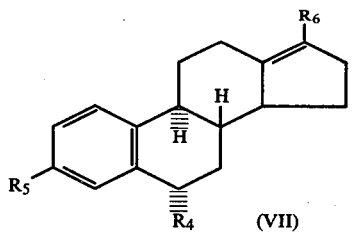

(VII)

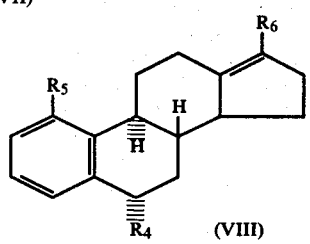

(VIII)

which may be written in the shorthand notation

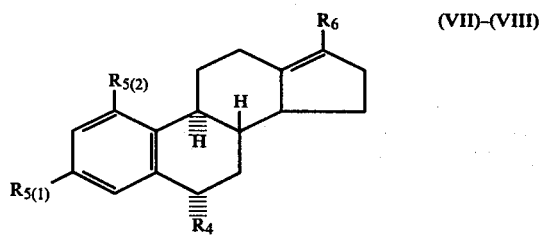

(VII)–(VIII)

wherein $R_4$ and $R_5$ have the meanings above and wherein one of $R_{5(1)}$ and $R_{5(2)}$ is $R_5$ and the other is H, and wherein $R_6$ is alkyl of from one to about four carbons.

When $R_5$ is H the resultant compounds are identical; when $R_5$ is not H, the cyclisation gives rise to two isomers in a ratio which may be strongly influenced as noted below by the cyclisation conditions and the choice of the substituent $R_5$.

Most preferably, in compounds (VI)–(VIII), one of $R_1$ and $R_2$ is H and the other $CH_3$, $R_3$ is OH, $R_4$ is $CH_3$ or $OCH_3$, $R_5$ is $OCH_3$, H or trialkylsilyloxy and $R_6$ is $CH_3$.

DESCRIPTION OF THE PREFERRED EMBODIMENTS

The cyclisation substrates of formula VI are novel compounds, which may be prepared by reactions which are themselves known to those skilled in the art. The invention therefore is characterized by the preparation of novel compounds with the general formula VI which are useful intermediates for preparing 6α-substituted steroidal compounds. The invention is also characterized by the cyclisation of the novel cyclisation substrates to steroid compounds, pseudo-equatorially substituted in position 6 and having the formulae VII and VIII. The 6α-substituted steroid compounds thus obtained are important starting materials for preparing biologically active 6α-substituted steroids.

As is shown in the FLOW DIAGRAM herewith, the cyclisation substrate VI may, for example, be prepared by a series of steps starting with step (a), condensing a β-$R_4$-β-arylpropanal (IX) with an ω-$R_2$-5,5,8,8-tetra-alkoxyoctylidenetriarylphosphorane (Wittig reagent X) or the tetra-alkylthioanalogue thereof under conditions which favor the (E)-configuration (Wittig-Schlosser reaction; see, for example, the German Pat. No. 1,270,545 and German Pat. No. 1,279,678, and 5 ANGEW. Chemie, Int. Ed. 126, (1966)).

The (E)-olefine-diketal (XI) obtained is hydrolysed in step (b) under weakly acid conditions to a 1-$R_4$-1-aryl-8,11-dioxo-11-$R_2$-3-undecene (XII), after which the dioxo compound is condensed in step (c) to a 2-(6'-$R_4$-6'-aryl-3'-hexenyl)-3-$R_2$-2-cyclopenten-1-one (XIII). In step (d) when $R_2$ is alkyl of one to four carbons, the ketone obtained is reduced to an alcohol or, when $R_2$=H, the ketone is caused to react with a compound $R_1$Li or $R_1$Mg-halogen, where $R_1$ is alkyl of one to four carbons, to give a tertiary alcohol. The OH-group is optionally further converted to an ester or ether group.

The cyclisation substrate thus obtained is subsequently cyclised in step (e) under acid conditions with a Lewis acid to a tetracyclic compound with a pseudo-equatorial $R_4$-substituent.

A protic or aprotic Lewis acid is used in the cyclisation (step e) and the reaction is performed in a suitable non-nucleophilic protic or aprotic solvent. Examples of suitable solvents are formic acid, acetic acid, trifluoroacetic acid, trifluoro-ethanol, benzene, saturated hydrocarbons such as pentane, hexane, cyclohexane, and halogenated hydrocarbons such as dichloromethane.

Examples of protic Lewis acids are carboxylic acids having a pK (20° C.) of less than about 4, preferably less than about 2, for example, trifluoro-acetic acid, trichloroacetic acid. These protic acids are used in an amount of at least 0.1 mol per mol cyclisation substrate. Examples of aprotic Lewis acids are tin chloride, titanium tetrachloride, zinc chloride, zinc bromide, boron trifluoride. Aprotic Lewis acids are preferred, in amounts of about 0.1 to 10 mol per mol cyclisation substrate, preferably 0.5 to 5 mol per mol cyclisation substrate.

The cyclisation reaction is usually performed at a temperature lower than about room temperature (22° C.-25° C.) and above −150° C., preferably at a temperature between +10° C. and −100° C.

The preparation is illustrated by the following reaction scheme:

FLOW DIAGRAM

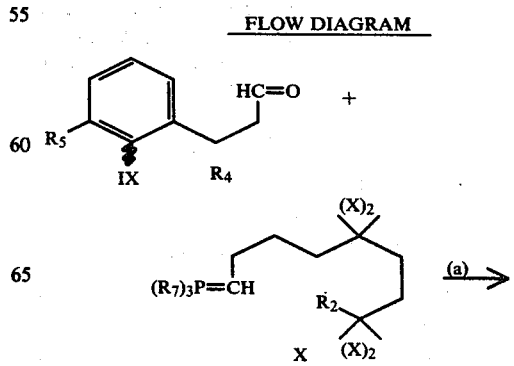

-continued
FLOW DIAGRAM

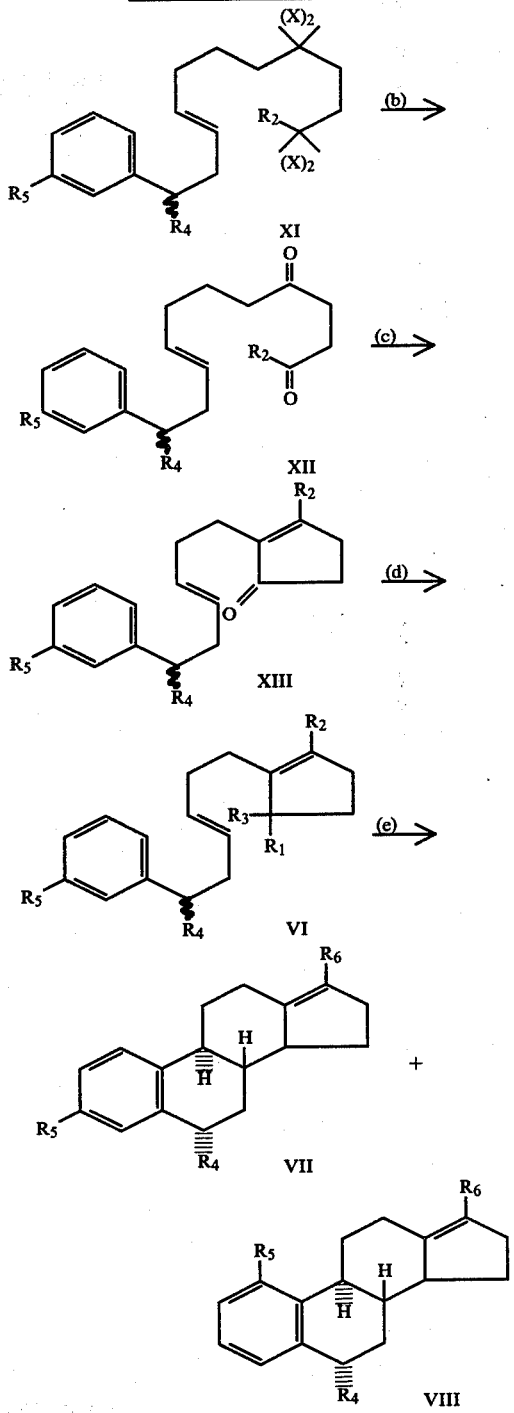

In this scheme, $R_1$, $R_2$, $R_3$, $R_4$, $R_5$ and $R_6$ have the meanings assigned above. $R_7$ is an aryl hydrocarbon group with about six or seven carbon atoms, preferably phenyl. X is an alkyl-chalcogen group, that is: alkoxy or alkylthio, each with about one to about four carbon atoms, preferably about one to about 2 carbon atoms. $(X)_2$ is preferably an alkylene-dichalcogen group, that is alkylene-dioxy or alkylene-dithio with about two to about three carbon atoms, for example, ethylene-dioxy, ethylenedithio, propylenedioxy.

In the preparation of the diketone with formula XII it is also possible to start from the $\beta$-$R_4$-$\beta$-arylaldehyde of formula IX and to allow this to react with a 4-(5'-$R_2$-2'-furyl)-butylidene-tri-arylphosphorane (XIV), after which the furyl-(E)-olefine (XV) thus obtained is hydrolysed with acid, according to the reaction scheme:

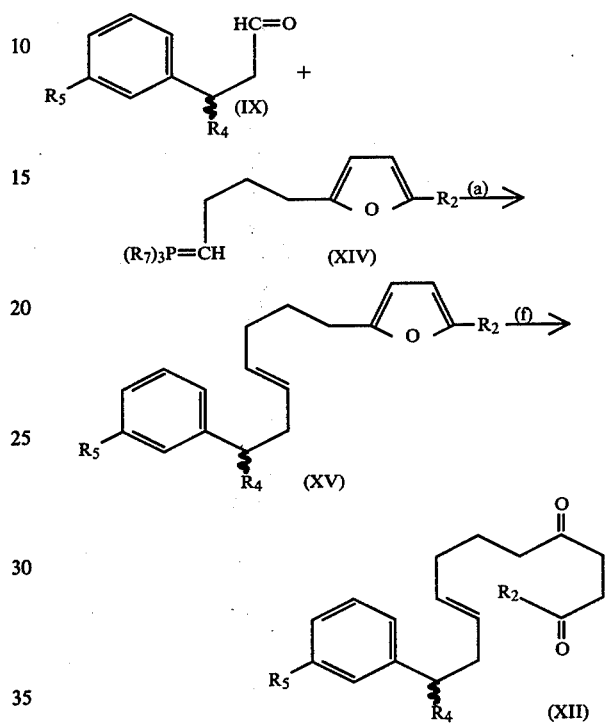

The hydrolysis with acid is preferably carried out with acetic acid in the presence of a catalytic amount of sulphuric acid, and at 100°–110° C.

The mixtures of "ortho" and "para" product ("ortho"=VIII=A-aromatic steroid substituted in the 1-position; "para"=VII=A-aromatic steroid substituted in the 3-position) obtained in the cyclisation step (e) can be separated in the usual way, for example, by chromatography or by crystallization.

Racemates of intermediates or end products may be resolved into the optical antipodes in the usual way.

As to the reaction steps (a)–(e) the following additional information can be given:

Reaction step (a) is usually carried out at a temperature between about −100° C. and about 0° C., preferably between about −75° C. and about −25° C. The solvent is usually an etheric solvent, such as diethyl ether, tetrahydrofuran and mixtures thereof. A preferred solvent is an 1:1 mixture of diethyl ether and tetrahydrofuran.

Reaction step (b) is usually carried out at a temperature between about 20° C. and 80° C., preferably between about 50° C. and 60° C. The solvent may be an etheric solvent, such as dimethoxyethane, or a mixture of water and an alcohol, such as ethanol. An 1:2 mixture of water and ethanol containing between 5 and 10 mmol HCl per liter, is very suited.

Reaction step (c) is usually carried out between about 60° C. and 80° C., preferably at about 80° C. The solvent is the same as used in step (b). An 1:2 mixture of water and ethanol containing between 5 and 10 mmol NaOH or an equivalent amount of KOH or trimethylbenzylammoniumhydroxide is very suited.

Reaction step (d): The reduction of the ketone to an alcohol is carried out with a complex metallic hydride, such as lithiumaluminiumhydride, di-isobutyl-aluminiumhydride, sodium-di-isobutylboronhydride, at a temperature between about −50° C. and 0° C., preferably between about −25° C. and 0° C. The reaction of the ketone with a compound $R_1Li$ or $R_1Mghalogen$ is usually carried out at a temperature between −70° C. and 0° C., preferably between −70° C. and −20° C. The solvent is usually an etheric solvent, preferably diethyl ether.

The reaction steps (a), (d), and (e) are preferably carried out in an inert atmosphere (nitrogen or argon blanket).

Reaction step (e): When using a protic solvent, preferably a protic Lewis acid is used. A protic solvent, such as formic acid, trifluoro-acetic acid, trifluoroethanol, may also serve as protic Lewis acid. An aprotic solvent may be combined with either a protic Lewis acid or an aprotic Lewis acid.

The following observations may be made with respect to the substituents $R_1$ to $R_6$ inclusive:

$R_1$ or $R_2$ is usually methyl or ethyl, preferably methyl, while the other substituent is H. As a leaving group, $R_3$ is generally alkoxy of one to four carbons, for example, methoxy; alkoxyalkoxy of two to four carbons, for example methoxymethoxy, 1'-ethoxyethoxy; carboxyacyloxy of one to seven carbons, for example acetoxy, propionyloxy, butyroxy, pivaloyloxy, valeryloxy, benzoyloxy, or trimethylsilyloxy.

$R_4$ is (1) a hydrocarbyl group of one to four carbons, optionally substituted by one or more halogens (preferably chlorine) or alkoxy of one to two carbons, preferably methoxy, (2) halogen, preferably fluorine or chlorine, or (3) alkoxy of one to four carbons, preferably methoxy.

By hydrocarbyl we mean a monovalent hydrocarbon radical selected from the saturated or unsaturated aliphatic, alicyclic or aliphatic moieties of one to four carbons.

Examples of optionally substituted hydrocarbyl groups for $R_4$ are methyl, ethyl, butyl, chloromethyl, methoxymethyl, allyl, 2'-chloroallyl.

It should be noted that it is not necessary for the substituent $R_4$ to be already present in its definitive form in the aldehyde of formula IX used as starting material. The reaction steps (a) to (d) inclusive may be alternated at the appropriate moment with a modification of $R_4$, or the substituent $R_4$ may optionally be modified in the cyclisation substrate immediately before the cyclisation. This means that the substituent $R_4$ in the formulae VI, IX, XI, XII, XIII and XV may also be a group which can readily be converted into one of the groups indicated previously for $R_4$, for example a hydroxy group which is converted in the usual way into F, Cl or alkoxy of from one to four at a suitable moment, but in any case before the cyclisation.

$R_5$ is preferably an optionally esterified or etherified hydroxy group, for example hydroxy, hydrocarbyloxy of one to eight carbons, such as methoxy, ethoxy, cyclopentoxy, cyclohexenyloxy, benzyloxy; α-alkoxyalkoxy of two to four carbons, such as methoxymethoxy, α-ethoxyethoxy; trimethylsilyloxy or tetrahydropyranyloxy, carboxyacyloxy of one to seven carbons, such as acetoxy, pivaloyloxy or benzoyloxy.

If $R_5$ is an oxy group then the two orthopositions and the para position with respect to $R_5$ are activated in the cyclisation. Steric factors prevent reaction at one of the ortho positions, and two products may therefore be formed, as indicated above by formulae VII and VIII. As previously noted, the ratio in which these two products are formed can be considerably displaced in favor of one of the products by means of a suitable and predetermined choice of $R_5$. If, for example, $R_5$ is trimethylsilyloxy, then the "para" product predominates over the "ortho" product.

If use is made as starting material of a β-arylaldehyde with $R_5$ being a "protected" hydroxy group, the "protecting group" may be maintained during the various reaction steps, but it may also be modified. Certain "protecting groups" are preferred for some reaction steps while other "protecting groups" are preferred for other reaction steps, for example in the steps (a) and (b) $R_5$ is preferably methoxy or methoxymethoxy. In steps (c) and (d) $R_5$ can remain in a hydroxy group without causing problems while in step (e) $R_5$ is preferably trimethylsilyloxy if the "para" product is primarily desired. The "para" product is specifically of importance since it may be used for the preparation of natural steroids.

The cyclisation substrate VI contains two asymmetric centers, to wit, the carbon atom carrying the substituent $R_1$, and the carbon atom carrying the substituent $R_4$. The stereochemistry of the cyclisation product proves to be governed predominantly by the latter center. In the cyclisation product, the substituent $R_4$ proves surprisingly to be present mainly in the pseudo-equatorial position. If a racemic cyclisation substrate is used as starting material, i.e., a substrate with equal amounts of the (R)-$R_4$ substituted and the (S)-$R_4$ substituted compound, a racemic tetracyclic product consisting of 2 enantiomers is formed, while on the grounds of the two asymmetric centers, without optical induction four stereo-isomers should have been formed in equal quantities. That the asymmetric center with the substituent $R_1$ has little or no influence on the stereochemistry of the end product is evident from the fact that the (S)-$R_1$-(S)-$R_4$ substituted cyclisation substrate gives the same $R_4$-pseudo-equatorial substituted cyclisation product as the (R)-$R_1$-(S)-$R_4$ substituted cyclisation substrate. For example, both 1(S)-3-methyl-2-[6'(S)-methyl-6'-(m-methoxyphenyl)-3'(E)-hexenyl]-2-cyclopentenol and 1(R)-3-methyl-2-[6'-(S)-methyl-6'-(m-methoxyphenyl)-3'(E)-hexenyl]-2-cyclopentenol give the natural 3-methoxy-6α-methyl-$\Delta^{1,3,5(10),13(17)}$-gonatetraene on cyclisation.

Formula VI indicates that the substituent $R_4$ may occupy the (R) configuration or the (S) configuration. If use is made of the racemate as cyclisation substrate, and the ortho/para isomerism of the aromatic ring is neglected, the cyclisation results in a racemate of $R_4$ pseudo-equatorial substituted steroid compound with formula VII. If the reaction commences with an optically active cyclisation substrate, for example the (S)-$R_4$ compound ($R_4$ being $CH_3$), an optically active compound of formula VII is formed, i.e., a natural 6α-$CH_3$-$\Delta^{1,3,5(10),13(17)}$-gonatetraene.

By epoxidising this 13(17)-olefin, preferably by conversion to a 13,17-halohydrin, in particular a chlorohydrin or bromohydrin, and treatment of the halohydrin with a base, the 13α,17α-epoxy compound of formula XVI is formed. (If the epoxidation is effected directly with a peracid, the 13β,17β-epoxy compound is formed). Opening of the epoxide ring under weakly acid conditions, preferably by using an aprotic Lewis acid, for example BF₃/di-ethyl ether, induces migration of the substituent R₆ from position 17 to position 13, such that the 13β-R₆-17-ketone of formula XVII if formed from the α-epoxide (in the same way, the β-epoxide gives the 13α-R₆-17-ketone):

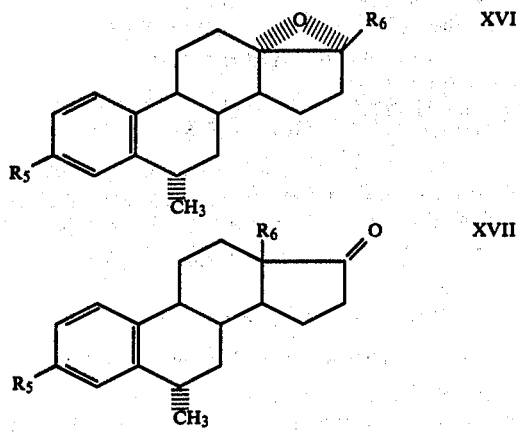

In this way, when $R_5$=methoxy and $R_6$=methyl, the 3-methyl ether of 6α-methyl-oestrone is obtained. In a corresponding fashion, the antipode can be converted into the ent-3-$R_5$-6α-$R_4$-13β-$R_6$-$\Delta^{1,3,5(10)}$-gonatrien-17-one.

The conversion of the $\Delta^{13(17)}$-olefine into the 13,17-halohydrin is carried out with a N-halo-carbonamide or -sulfonamide, such as N-chloro- or N-bromo-succinimide, N-chloro-toluenesulfonamide, in a mixture of water and an organic solvent, such as t-butanol, tetrahydrofuran, dimethoxyethane. Treatment of the 13,17-halohydrin with a base is carried out with an aqueous NaOH- or KOH-solution. The opening of the epoxide ring is carried out in an apolar aprotic solvent, for example hydrocarbons, such as benzene, or halogenated hydrocarbons, such as methylene chloride.

Thus, the present invention provides novel cyclisation substrates which give on cyclisation novel 6α-substituted steroidal cyclisation products. The cyclisation substrates as well as the cyclisation products are important novel intermediates for preparing well-known biologically active 6α-substituted steroids.

Although the invention has been described with reference to specific embodiments above, numerous variations and modifications will become evident to those skilled in the art, without departing from the scope and spirit of the invention as described above, defined in the appended claims, and as shown in the following Examples:

EXAMPLE I

Preparation of dl-3-(m-methoxyphenyl)-butanal
(Formula IX, $R_4$=CH₃; $R_5$=OCH₃)

(a) Under a N₂ blanket, a solution of lithium dimethylcuprate was prepared at 0° C. from cuprous iodide (7.6 g, 0.04 mol) and a solution of methyl-lithium in ether (80 ml, 1 M, 0.08 mol). A solution of methyl m-methoxycinnamate (4.8 g, 0.025 mol) in ether (20 ml) was then added dropwise and the reaction mixture was stirred for 1 hour at 0° C. A large volume of water was cautiously added, after which the ether layer was separated, dried (anhydrous Na₂SO₄) and evaporated to dryness. The residue was chromatographed on silica gel (100 g) with hexane/ethyl acetate (80:20) as eluent, giving 3.65 g methyl β-(m-methoxyphenyl)-butyrate (68% yield by weight).

(b) The product from Example I(a) (2,08 g, 0.010 mol) was dissolved in dry toluene (20 ml). The solution was cooled to −70° C., after which a solution of di-isobutyl aluminium hydride in toluene (10 ml, 1.2 M, 0.012 mol) was slowly added dropwise. After stirring for 15 minutes at −70° C., the reaction mixture was poured into 40 ml 2 N sulphuric acid. The toluene layer was separated and dried (anhydrous Na₂SO₄). Removal of solvent by evaporation, followed by chromatography on silica gel (50 g) with hexane/ethyl acetate 90:10 gave 1.28 g pure aldehyde (72% yield).

EXAMPLE II

Preparation of dl-(E)-2-(m-methoxyphenyl)-9,12-bis(ethylenedioxy)-4-tridecene (Formula XI, $R_2$=CH₃; $R_4$=CH₃; $R_5$=OCH₃; (X)₂=ethylene-dioxy). Reaction (a)

A solution of phenyl-lithium in ether (11 ml, 1 M, 0.011 mol) was added dropwise under nitrogen blanket to a stirred suspension of 5,8-bis(ethylene-dioxy)-nonyl-triphenyl phosphonium iodide (6.32 g, 0.01 mol) in 20 ml dry tetrahydrofuran, surrounded and cooled in ice. The red solution was stirred without cooling for a further 15 minutes and was then cooled to −70° C. A solution of dl-3-(m-methoxyphenyl)-butanal (1.6 g, 9 mmol) from Example I in dry tetrahydrofuran (5 ml) was added dropwise, followed after 5 minutes by a second quantity of phenyllithium (18 ml, 1 M, 0.018 mol).

The red solution obtained was warmed to −30° C. After 5 minutes, 1 ml methanol was added dropwise, followed by 50 ml water. The mixture was extracted with ether (3×25 ml). The extracts were dried (anhydrous Na₂SO₄) and evaporated to dryness. The residue was chromatographed on silica gel (70 g) with hexane/ethyl acetate 80:20 by weight, giving 2.89 g product as a colorless oil (79% yield).

EXAMPLE III

Preparation of dl-3-methyl-2-[(E)-6'-(m-methoxyphenyl)-3'-heptenyl]-2-cyclopentenone (Formula XIII, $R_2$=CH₃; $R_4$=CH₃; $R_5$=OCH₃). Reactions (b) and (c).

A solution of the Wittig product from Example II (2.02 g, 0.005 mol) in 60 ml 95% by weight ethanol and 30 ml 0.2 N hydrochloric acid was warmed at 55°-60° C. for 1½ hours, after which 8 ml 2 N potassium hydroxide was added and the reaction mixture was heated under reflux for 2 hours.

The solution was then reduced under vacuum to a bulk of about 40 ml and extracted with ether. The extracts were dried over anhydrous Na₂SO₄ and evaporated to dryness giving a residue which was chromatographed on silica gel (50 g) with hexane/ethyl acetate 80:20. The product was obtained as a colourless oil (1.26 g, 84% yield).

EXAMPLE IV

Preparation of
dl-3-methyl-2-[(E)-6'-(m-methoxyphenyl)-3'-heptenyl]-2-cyclopentenol (Formula VI, $R_1$=H; $R_2$=$CH_3$; $R_3$=OH; $R_4$=$CH_3$; $R_5$=$OCH_3$). Reaction (d)

Lithium aluminium hydride (0.20 g, 5.2 mmol) was added at about −20° C. to a solution of the product from Example III (0.79 g, 2.65 mmol) in dry ether (25 ml). The mixture was warmed with stirring to 0° C. over a period of about 30 minutes. The excess hydride was decomposed by cautious addition of saturated sodium sulphate solution. The ether layer was decanted from the precipitate formed, and the latter was washed twice with ether. The combined ether solutions was evaporated to dryness, giving 0.79 g (99% yield) of a product which was immediately used for the following reaction step.

EXAMPLE V

Preparation of
dl-1-and-3-methoxy-6α,17-dimethyl-$\Delta^{1,3,5(10),13(17)}$-gonatetraene. (Formulae VII and VIII, $R_4$=$CH_3$; $R_5$=$OCH_3$; $R_6$=$CH_3$. Reaction (e)

The cyclopentenol from Example IV (0.79 g, 2.63 mmol), now dissolved in dry dichloromethane (10 ml), was added dropwise at −70° C. to a solution of stannic chloride (0.8 ml) in dry dichloromethane (30 ml). The mixture thus obtained was stirred for about 30 minutes at −70° C. A solution of NaOH (2.0 g) in 10 ml 80% ethanol was then added dropwise in such a way that the temperature did not rise above −60° C. The reaction mixture was washed with water and dried over anhydrous $K_2CO_3$. The solvent was removed by evaporation and the residue was chromatographed on silica gel (30 g) with hexane/toluene 80:20, giving first the 1-methoxy-6α-methyl isomer (72 mg, 9.6% yield, melting point 87°–97° C. The 3-methoxy-6α-methyl isomer, containing about 10% of the 6β-methyl isomer, was then eluted (353 mg, 47% yield, m.p. 37°–42° C.).

EXAMPLE VI

Preparation of dl-6α-methyloestrone, methyl ether. (Formula XVII, $R_5$=$OCH_3$; $R_6$=$CH_3$).

N-chlorosuccinimide (154 mg, 1.16 mmol) was added to a solution of 3-methoxy-6αmethyl-17-methyl-1,3,5,(10),13(17)-gonatetraene (from Example V, 165 mg, 0.58 mmol) in t-butanol/water 9:1 (15 ml). The mixture was stirred for 30 minutes at 20° C., after which sodium bisulphite (0.10 g) in water (1 ml) and 5 ml 10% KOH solution were added. The solution was stirred for 45 minutes at room temperature and was then mixed with 50 ml hexane, whereupon the aqueous layer separated and was removed, and the organic layer was then evaporated to dryness under vacuum.

The residue, consisting of the 13,17α-epoxy derivative, was taken up in toluene and treated with boron trifluoride etherate (1 ml) for 1 minute at room temperature.

The dark red reaction mixture was washed to neturality with potassium carbonate solution. The residue remaining after drying (anhydrous $K_2CO_3$) and removal of solvent by evaporation was chromatographed on silica gel (20 g) with dichloromethane. The product (36 mg, 21% yield) was obtained as a light yellow oil.

EXAMPLE VII

Preparation of dl-6α-methyloestradiol, 3-methyl ether.

Reduction of the product from Example VII (10 mg) with lithium aluminium hydride (10 mg) in ether (1 ml) gave, after working up and crystallization from ether, 9 mg of the 3-methyl ether of dl-6α-methyl-oestradiol, melting point 173°–174° C. (yield 90%).

EXAMPLE VIII

Preparation of dl-6α-18-dimethyloestrone, 3-methylether (Formula XVII, $R_5$=$OCH_3$, $R_6$=$C_2H_5$).

Starting from dl-3-(m-methoxyphenyl)-butanal and 5,8-bis(ethylene-dioxy)-decyl-triphenylphosphonium iodide, the 3-methyl ether of dl-6α,18-dimethyloestrone was obtained in a way analogous to that described in Examples II-VI.

EXAMPLE IX

Preparation of 2-(4-bromobutyl)furan

A solution of furan (23.8 g, 0.35 mol) in dry tetrahydrofuran (150 ml) was cooled to −15° C., after which a solution of n-butyllithium in hexane (150 ml, 2.2 M, 0.33 mol) was added dropwise under nitrogen. The whole was stirred for a further 2½ hours at 0° C. The solution thus obtained was subsequently added under nitrogen blanket during a period of about 1 hour to a solution of 1,4-dibromobutane (150 g, 0.7 mol) in dry tetrahydrofuran (225 ml), cooled to −25° C.

This mixture was stirred for a further 3 hours at 0° C. and for 15 hours at room temperature. Saturated common salt solution (200 ml) was then added and the organic layer was separated and dried (anhydrous $MgSO_4$). Distillation under vacuum with the aid of a Vigreux TM set-up gave 44 g pure product (66% by weight yield).

EXAMPLE X

Preparation of 8-bromo-1,4-bis(ethylene-dioxy)octane

A mixture of 2-(4-bromobutyl)furan (20.3 g, 0.1 mol), benzene (120 ml), glycol (120 ml) concentrated sulphuric acid (12 ml) and tetra-n-butylammonium bromide (1.2 g) was refluxed for 96 hours with the aid of an azeotropic water separator. The reaction mixture was cooled and the benzene layer was separated. The glycol-layer was washed with a few portions of benzene after which the combined benzene layers were washed to neutrality with saturated sodium bicarbonate solution. The benzene-solution was dried over anhydrous $MgSO_4$ and evaporated to dryness. The residue was chromatographed on silica gel (200 g) with hexane/ethyl acetate 8:2, giving 7.5 g product (24% yield) in the form of a colorless oil.

EXAMPLE XI

Preparation of 8-iodo-1,4-bis(ethylene-dioxy)octane.

The bromide from Example X (7.5 g, 0.024 mol) was dissolved in butan-2-one, after which powdered potassium iodide (6.8 g, 0.041 mol) and pyridine (0.2 ml) were added. The mixture was boiled under reflux for 1½ hours after which it was mixed with ether and filtered. Evaporation to dryness gave 8.2 g product (95% by weight yield).

EXAMPLE XII

Preparation of 5,8-bis(ethylene-dioxy)octyl-triphenylphosphonium iodide.

The iodide from Example XI (8.2 g, 0.023 mol) and triphenylphosphine (10 g, 0.038 mol) were dissolved in benzene (70 ml). The solution was boiled with stirring for 16 hours. After cooling, the benzene layer was decanted and the viscous residue was dissolved in a little acetone. Addition of ether gave 5.01 g crystalline product (35% yield), melting point 102°–104° C., while further dilution of the mother liquor with ether gave another 6.0 g (42% by weight yield) of an oily product.

EXAMPLE XIII

Preparation of dl-(E)-2-(m-methoxyphenyl)-9,12-bis(ethylene-dioxy)-4-dodecene. (Formula XI, $R_2$=H; $R_4$=CH$_3$; $R_5$=OCH$_3$; $(X)_2$=ethylene-dioxy). Reaction (a).

5,8-bis(ethylene-dioxy)octyl-triphenylphosphonium iodide (3.1 g, 0.005 mol) was reacted with dl-3-(m-methoxyphenyl)butanol (0.89 g, 0.005 mol) under conditions similar to that described in Example II, giving 1.1 g pure product (57% by weight yield).

EXAMPLE XIV

Preparation of dl-2-[(E)-6'-(m-methoxyphenyl)-3'-heptenyl]-2-cyclopentenone. (Formula XIII, $R_2$=H; $R_4$=CH$_3$; $R_5$=OCH$_3$). Reactions (b) and (c).

The product from Example XIII (1.1 g, 2.8 mol) was dissolved in a mixture of dimethoxy-ethane (110 ml) and 1 N hydrochloric acid (36 ml). The solution was warmed at 50°–60° C. under nitrogen for 2½ hours, cooled and reduced to a bulk of about 50 ml by evaporation under vacuum. The residue was extracted with ether, three times.

The ether extracts were dried (anhydrous Na$_2$SO$_4$) and evaporated to dryness. The residue (0.85 g), dissolved in a mixture of 90 ml 95% ethanol and 22.5 ml 0.2 N potassium hydroxide, was heated at 50° C. for 6 hours under nitrogen. The product was isolated under conditions similar to that described in Example III, giving 0.32 g pure product (40% yield) in the form of a colorless oil.

EXAMPLE XV

Preparation of dl-2-[(E)-6'-(m-methoxyphenyl)-3'-heptenyl]-1-methyl-2-cyclopenten-1-ol (Formula VI, $R_1$=CH$_3$; $R_2$=H; $R_3$=OH; $R_4$=CH$_3$; $R_5$=OCH$_3$). Reaction (d)

The product from Example XIV (0.284 g, 1 mmol) was dissolved in dry ether (15 ml) and the resultant solution was cooled under nitrogen to −70° C. Excess methyl-lithium in ether (1.5 ml, 2 M, 3 mmol) was added. After stirring for a further 10 minutes at −70° C., a few drops of saturated sodium sulphate solution were added. The mixture obtained was warmed, filtered, and evaporated to dryness. The product was obtained in quantitative yield (0.30 g) as a colorless oil.

EXAMPLE XVI

Preparation of dl-1-methoxy- and dl-3-methoxy-6α,17-dimethyl-$\Delta^{1,3,5(10),13(17)}$-gonatetraene. (Formulae VII and VIII, $R_4$=CH$_3$; $R_5$=OCH$_3$; $R_6$=CH$_3$). Reaction (e)

The product from Example XV (0.30 g) was cyclised to the 1-methoxy-6α-methyl compound (0.07 g) and the 3-methoxy-6α-methyl compound (0.08 g) under conditions similar to that described in Example V.

EXAMPLE XVII

Preparation of dl-(E)-2-(m-hydroxyphenyl)-9,12-bis(ethylene-dioxy)-4-tridecene. (Formula XI, $R_2$=CH$_3$; $R_4$=CH$_3$; $R_5$=OH; $(X)_2$=ethylene-dioxy).

A solution of (E)-2-(m-methoxyphenyl)-9,12-bis(ethylene-dioxy)-4-tridecene (1.21 g, 0.003 mol; see Example II) and KOH (1.6 g) in tri-ethylene glycol (16 ml) was heated for 2 hours at 200° C. The reaction mixture was cooled, diluted with water, and acidified with 4 N hydrochloric acid, after which it was extracted with chloroform (3×20 ml). The extracts were dried (anhydrous Na$_2$SO$_4$) and evaporated to dryness. The residue was chromatographed on 35 g silica gel and hexane/ethyl acetate 80:20 followed by 60:40.

In this way 0.55 g starting material was obtained followed by 0.41 g product (colourless oil). Yield=64% by weight on basis of converted starting-material.

EXAMPLE XVIII

Preparation of dl-3-methyl-2-[(E)-6'-(m-hydroxyphenyl)-3'-heptenyl]-2-cyclopentenone. (Formula XIII, $R_2$=CH$_3$; $R_4$=CH$_3$; $R_5$=OH).

The product from Example XVII (0.41 g) was converted in a way analogous to that described in Example III. The product was obtained as a colorless oil, 0.25 g, 84% yield.

EXAMPLE XIX

Preparation of dl-3-methyl-2-[(E)-6'-(m-t.butyldimethylsilyloxyphenyl)-3'-heptenyl]-2-cyclopentenone. (Formula XIII, $R_2$=CH$_3$; $R_4$=CH$_3$; $R_5$×t-butyl-dimethylsilyloxy).

The product from Example XVIII (0.25 g, 0.9 mmol) was dissolved in dry dimethylformamide (1 ml). Imidazole (0.48 g, 7 mmol) and t-butyldimethyl-chlorosilane (0.30 g, 2 mmol) were added. After stirring for 3 hours at 38° C., water was added and the mixture obtained was extracted with ether. The extract was dried (anhydrous Na$_2$SO$_4$) and evaporated to dryness. The residue was purified by chromatography (silica gel, hexane/ethyl acetate 80:20), giving 0.30 g product (95% yield by weight) in the form of an oil.

EXAMPLE XX dl-1- and 3-butyldimethylsilyloxy-6α,17-dimethyl-$\Delta^{1,3,5(10),13(17)}$-gonatetraene (Formulae VII and VIII, $R_4$=CH$_3$; $R_5$=t-butyldimethylsilyloxy; $R_6$=CH$_3$).

The product from Example XIX (0.30 g) was reduced in a way analogous to that described in Example IV. The cyclopentenol obtained was subsequently cyclised under conditions similar to that described in Example V and the mixture of products thus obtained was separated by chromatography on silica gel with hexane, followed by hexane/toluene 9:1 by weight. In this way, the 1-silyloxy compound was first isolated (40 mg) followed by the 3-silyloxy compound (140 mg), both as oils.

EXAMPLE XXI

Preparation dl-3-(m-methoxyphenyl)-3-methoxy-propanal (Formula IX, $R_4=R_5=OCH_3$).

Methyl$\beta$-(m-methoxyphenyl)-$\beta$-hydroxy-propionate was reacted with methyl iodide/sodium hydride to give methyl-$\beta$-(m-methoxyphenyl)-$\beta$-methoxy-propionate, which was then reduced with $LiAlH_4$ in dry ether to give 3-(m-methoxyphenyl)-3-methoxy-propanol. This latter product was converted into 3-(m-methoxyphenyl)-3-methoxy-propanal by oxidation with pyridinium chlorochromate in dry dichloromethane.

EXAMPLE XXII

Preparation of dl-1,6$\alpha$- and -3,6$\alpha$-dimethoxy-17-methyl$\Delta^{1,3,5(10),13(17)}$-gonatetraene. (Formulae VII and VIII, $R_4=OCH_3$; $R_5=OCH_3$; $R_6=CH_3$)

Starting from 3-(m-methoxyphenyl)-3-methoxy-propanal and 5,8-bis(ethylenedioxy)nonyltriphenylphosphonium iodide, 1,6$\alpha$and 3,6$\alpha$-dimethoxy-17-methyl-$\Delta^{1,3,5(10),13(17)}$-gonatetraene were prepared in a way analogous to that described in Examples II - V. 1-Methoxyisomer, m.p. 115-119° C.; 3-methoxyisomer, m.p. 93°-97° C.

Physical constants of cyclisation substrates (cyclopentenols) and cyclisation products (6$\alpha$-substituted $\Delta^{1,3,5(10),13(17)}$-gonatetraenes) obtained in the above Examples:

The cyclopentenol of Example IV

Oil with $R_f$ (hexane/ethylacetate 6:4): 0.46 ($SiO_2$); NMR ($CCl_4$): $\delta$ 1.19 (d, J=7, ArCHCH$_3$), 1.58 (s, allylic CH$_3$), 3.71 (s, OCH$_3$), 4.50 (m, H at C-1), 5.32 (m, olefinic protons).

dl-3-Ethyl-2-[(E)-6'-(m-methoxyphenyl)-3'-heptenyl]-2-cyclopentenol (Formula VI, $R_1=H$; $R_2=C_2H_5$; $R_3=OH$; $R_4=CH_3$; $R_5=OCH_3$; intra Example VIII):

Oil with $R_f$ (hexane/ethylacetate 6:4): 0.47 ($SiO_2$); NMR (CDCl$_3$): $\delta$ 1.22 (d, J=7, ArCHCH$_3$), 0.91 and 1.97 (t, J=7 and q, J=7, C$_2$H$_5$), 3.80 (s, OCH$_3$), 4.5 (m, H at C-1), 5.3 (m, olefinic protons).

dl-1-Methoxy-6$\alpha$-methyl-17-ethyl-$\Delta^{1,3,5(10),13(17)}$-gonatetraene (Formula VII, $R_4=CH_3$; $R_5=OCH_3$; $R_6=C_2H_5$; intra Example VIII).

M.p. 62°-70° C.

dl-3-Methoxy-6$\alpha$-methyl-17-ethyl-$\Delta^{1,3,5(10),13(17)}$-gonatetraene (Formula VIII, $R_4=CH_3$; $R_5=OCH_3$; $R_6=C_2H_5$; intra Example VIII).

Oil with $R_f$ (hexane/toluene 7:3): 0.35; NMR (CDCl$_3$); $\delta$ 1.30 (d, J=6, 6$\alpha$-CH$_3$), 0.95 and 2.05 (t, J=7 and q, J=7, 17-C$_2$H$_5$), 3.76 (OCH$_3$).

The cyclopentenol of Example XV

Oil with $R_f$ (hexane/ethylacetate 8:2): 0.31 ($SiO_2$); NMR ($CCl_4$): $\delta$ 1.20 (d, J=7, ArCHCH$_3$), 1.25 (s, C-1-methyl); 3.72 (s, OCH$_3$), 5.1-5.5 (m, olefinic protons).

dl-3-Methyl-2-[(E)-6'-(m-t.butyldimethylsilyloxyphenyl)-3'-heptenyl]-2-cyclopentenol (Formula VI, $R_1=H$; $R_2=CH_3$; $R_3=OH$; $R_4=CH_3$; $R_5=t.butyldimethylsilyloxy$; intra Example XX).

Oil with $R_f$ (hexane/ethylacetate 8:2): 0.27 ($SiO_2$); NMR ($CCl_4$): $\delta$ 0.17 (s, Si(CH$_3$)$_2$), 0.97 (s, Si-t-butyl), 1.19 (d, J=7, ArCHCH$_3$), 1.58 (s, allylic CH$_3$), 4.50 (m, H at C-1), 5.3 (m, olefinic protons).

The 1-silyloxy-gonatetraene of Example XX

Oil with $R_f$ (hexane/toluene 9:1): 0.46 ($SiO_2$); NMR (CDCl$_3$): $\delta$ 0.15 (s, Si-CH$_3$), 0.23 (s, Si-CH$_3$), 1.0 (s, Si-t.butyl), 1.26 (d, J=6, 6$\alpha$-CH$_3$), 1.64 (s, 17-CH$_3$), 3.79 (OCH$_3$).

The 3-silyloxy-gonatetraene of Example XX

Oil with $R_f$ (hexane/toluene 9:1): 0.35 ($SiO_2$), NMR (CDCl$_3$): $\delta$ 0.17 (s, Si(CH$_3$)$_2$), 0.97 (s, Si-t-butyl), 1.30 (d, J=6, 6$\alpha$-CH$_3$), 1.62 (s, 17-CH$_3$), 3.76 (OCH$_3$).

dl-3-Methyl-2-[(E)-6'-(m-methoxyphenyl)-6'-methoxy-3'-hexenyl]2-cyclopentenol (Formula VI, $R_1=H$, $R_2=CH_3$; $R_3=OH$; $R_4=OCH_3$; $R_5=OCH_3$; intra Example XXII):

Oil with $R_f$ (hexane/ethylacetate 6:4): 0.26 ($SiO_2$); NMR (CDCl$_3$): $\delta$ 1.60 (s, allylic CH$_3$), 3.38 (s, ArCHOCH$_3$), 3.79 (s, ArOCH$_3$), 4.5 (m, H at C-1), 4.9 (m, Ar-CH-), 5.3 (m, olefinic protons).

What is claimed is:

1. A compound of the formula:

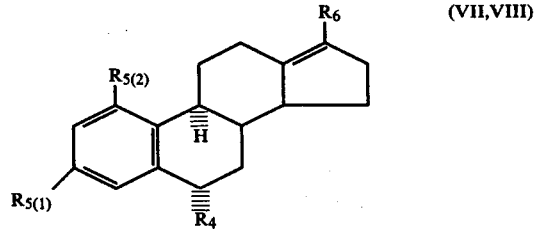

(VII,VIII)

wherein:
(a) $R_4$ is halogen, alkoxy of from one to four carbons, and hydrocarbyl of from one to four carbons substituted by one or more (1) halogens or (2) alkoxy moieties of from one to two carbons;

(b) $R_{5(1)}$ and $R_{5(2)}$ are each H, alkyl of one to six carbons, hydroxy, or an esterified or etherified moiety of (1) less than eight carbons selected from the group consisting of alkoxy, trialkylsilyloxy, aralkyloxy, cycloalkoxy, and heterocyclo-oxy radicals; (2) $\alpha$-alkoxyalkoxy of from two to four carbons, and (3) acyloxy of from one to seven carbons with the proviso that at least one of $R_{5(1)}$ and $R_{5(2)}$ is H; and (c) $R_6$ is alkyl of one to four carbons.

2. A compound of the formula:

3. A compound of the formula
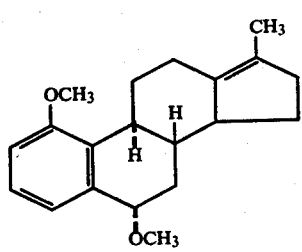
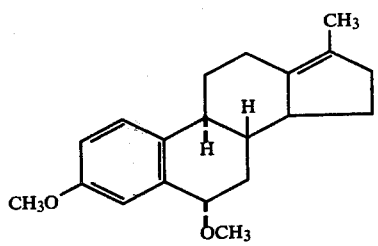
* * * * *